United States Patent [19]

Field et al.

[11] Patent Number: 4,883,890

[45] Date of Patent: Nov. 28, 1989

[54] UNSYMMETRICAL ORGANIC DISULFIDE COMPOUNDS USEFUL AS ANTIRADIATION AGENTS

[75] Inventors: Lamar Field, Nashville, Tenn.; Hikmat A. Musallam, Damascus, Md.; Jeffrey D. Macke, Ft. Mitchell, Ky.; Pramod K. Srivastava, Varanasi, India

[73] Assignee: Vanderbilt University, Nashville, Tenn.

[21] Appl. No.: 228,010

[22] Filed: Aug. 3, 1988

Related U.S. Application Data

[62] Division of Ser. No. 907,882, Sep. 16, 1986.

[51] Int. Cl.$^4$ .................................................. C07C 145/00
[52] U.S. Cl. ........................................ 558/61; 562/125
[58] Field of Search ........................... 558/61; 260/513.7

[56] References Cited

U.S. PATENT DOCUMENTS 3,723,513  3/1973  Field et al. .................. 260/513.7

OTHER PUBLICATIONS

Srivastava, et al., J. Med. Chem., 18, 798 (1975).
Sristava, et al., J. Chem. & Engin. Data, 31, 252 (1986).
Field, et al., J. Med. Chem. 15, 312 (1972).
Bowman, et al., Chem.-Biol. Interactions, 57, 161 (1986).

Primary Examiner—Nicky Chan
Attorney, Agent, or Firm—Tilton, Fallon, Lungmus & Chestnut

[57] ABSTRACT

Unsymmetrical organic disulfide sulfinate compounds, useful as an antiradiation agents, having the general formula:

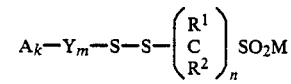

wherein A is one or of the following polar groups, OH, COOH, SO$_3$Na, —C(O)—, or derivatives such as esters and nonamino nitrogen derivatives such as amides or nitriles; k is an integer of one to eight; Y is a straight or substituted aliphatic chain having from two to eight carbon atoms which may have one or more S—S groups interposed therebetween; m signifies the number of carbon atoms in an aliphatic chain Y containing 2 to 8 carbon atoms which may have S—S interposed; aliphatic chain Y, substituted with one or more polar groups of the number k is attached to one of the two sulfur atoms shown. The second sulfur atom is attached through an aliphatic chain of 2 to 5 carbon atoms to the sulfinate function SO$_2$M wherein R$^1$ and R$^2$ may be hydrogen, aryl, cycloalkyl or various polar groups such as OH, COOH, SO$_3$Na, —C(O)—, or derivatives such as esters and nonamino derivatives such as amides or nitriles. The system

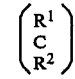

also may comprise an aromatic ring; n may be the integers 2 through 6; M of the sulfinate function is hydrogen, a metallic element selected from group 1 A of the Periodic Table such as Li, Na, or K, or the equivalent R$_4$N+; or an organic group such as a straight or substituted aliphatic chain having up to 4 carbon atoms, designed to promote stability. The synthesis of the compounds occurs by subjecting 1,1-dioxides of cyclic disulfides to the action of a thiolate ion, whereby cleavage is effected between the sulfur and sulfonyl units.

4 Claims, No Drawings

UNSYMMETRICAL ORGANIC DISULFIDE COMPOUNDS USEFUL AS ANTIRADIATION AGENTS

This invention was made with Government support under contract Number DAMD17-85-C-5181 awarded by the United States Army Medical Research Acquisition Activity.

This is a division of application U.S. Ser. No. 907,882 filed Sept. 16, 1986.

BACKGROUND OF THE INVENTION

The present invention relates to new unsymmetrical organic disulfide compounds, which possess antiradiation properties, i.e. they protect mammals against otherwise lethal ionizing radiation. The invention relates also to the process of the synthesis of the compounds. Prior to the present invention, it generally was accepted that antiradiation compounds required the presence of nitrogen, such as an amine function, for activity. U.S. Pat. No. 3,723,513 discloses an organic disulfide compound having antiradiation properties having a nitrogen atom attached to an aliphatic chain having 2 or 3 carbon atoms that is connected through a chain of two sulfur atoms to a carbon chain terminated by a sulfinate group ($-SO_2M$). It has been believed that adverse biological effects are caused by the presence of the nitrogen as an amine. These effects can be avoided by producing antiradiation compounds without nitrogen as an amine. The unsymmetrical organic disulfides of the present invention possess antiradiation properties in the absence of any amino-nitrogen function.

SUMMARY OF THE INVENTION

The compounds of the present invention, which are protective against ionizing radiation, may be represented by the following general formula:

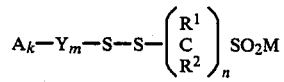

wherein A is one or more of the following polar groups, OH, COOH, $SO_3Na$, $-C(O)-$, or derivatives such as esters and nonamino nitrogen derivatives such as amides or nitriles; k is an integer of one to eight; Y is a straight or substituted aliphatic chain having from two to eight carbon atoms which may have one or more S-S groups interposed therebetween; m signifies the number of carbon atoms in an aliphatic chain Y containing 2 to 8 carbon atoms which may have S-S interposed; aliphatic chain Y, substituted with one or more polar groups of the number k is attached to one of the two sulfur atoms shown. The second sulfur atom is attached through an aliphatic chain of 2 to 5 carbon atoms to the sulfinate function $SO_2M$ wherein $R^1$ and $R^2$ may be hydrogen, aryl, cycloalkyl or various polar groups such as OH, COOH, $SO_3Na$, $-C(O)-$, or derivatives such as esters and nonamino derivatives such as amides or nitriles. The system

also may comprise an aromatic ring; n may be the integers 2 through 6; M of the sulfinate function is hydrogen, a metallic element selected from group 1A of the Periodic Table such as Li, Na, or K, or the equivalent $R_4N+$; or an organic group such as a straight or substituted aliphatic chain having up to 4 carbon atoms, designed to promote stability. The synthesis of the compounds occurs by subjecting 1,1-dioxides of cyclic disulfides to the action of a thiolate ion, whereby cleavage is effected between the sulfur and sulfonyl units.

DESCRIPTION OF THE PREFERRED EMBODIMENTS

In accordance with the invention, cyclic disulfides such as 1,2-dithiolane, 1,2-dithiane, and 1,2-dithiepane were first prepared from alpha, omega-alkane-dithiols. The carbon chain between the thiol groups may bear substituents. U.S. Pat. No. 3,723,513 describes the cyclization to the preferred disulfides and oxidation of the cyclic disulfides to 1,1-dioxides. The total preparation of the 1,1-dioxide is represented by the general formula as follows:

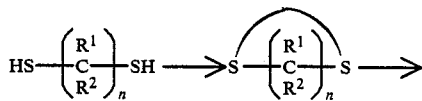

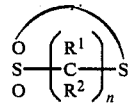

Continuing with the description of the invention, 1,2-dithiolane, 1,1-dioxide, or 1,2-dithiane 1,1-dioxide, or 1,2-dithiepane 1,1-dioxide was caused to react with a thiolate ion to produce disulfides containing a sulfinate moiety. The general sequence for these reactions is as follows:

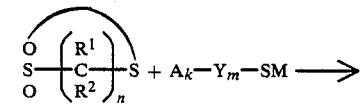

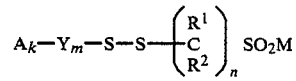

wherein A, Y, M, k, m, and n are as previously described except that M, in this instance, is not an "organic group such as a straight or substituted aliphatic chain having up to 4 carbon atoms" and $R^1$ and/or $R^2$ are polar or nonpolar substituents; as stated,

also may comprise an aromatic ring. A may be one or more polar functional groups which contain no nitrogen as an amine, such as OH, COOH, $SO_3Na$, $-C(O)-$ or derivatives such as esters and monamino nitrogen derivatives such as amides or nitriles. The final products of the invention resemble those of U.S. Pat. No. 3,723,513 but differ in the crucial respect that none contains a nitrogen atom as an amine but that all do contain a short chain substituted by one or more polar groups, which is attached to the SS linkage. Preferred embodiments of the present invention are represented by the formulations:

(A) $HOCH_2CH(OH)CH_2SS(CH_2)_4SO_2Na \cdot 1.15H_2O$
(B) $HO_2C(CH_2)_2SS(CH_2)_3SO_2Na \cdot 0.75H_2O$
(C) $HO_2C(CH_2)_2SS(CH_2)_4SO_2Na \cdot 0.75H_2O$
(D) $HO_2C(CH_2)_2SS(CH_2)_5SO_2Na \cdot 0.35H_2O$
(E) $NaO_2S(CH_2)_4SS(CH_2)_4SS(CH_2)_4SO_2Na \cdot 4H_2O$ Compounds of the present invention are conveniently prepared in accordance with the following general procedure.

GENERAL PROCEDURE

A solution of sodium (230 mg, 10.0 mg atoms) in 10 mL of MeOH was added dropwise during ca. 30 min to a mixture of 10.0 mmol of a cyclic disulfide 1,1-dioxide and 10.0 mmol of the appropriate thiol in methanol (50 mL) with constant stirring at 0°–5° C. A slight excess of the dioxide often was used, since any not consumed can be easily removed in the purification. After the addition was completed (usually about 15 minutes) and after the reaction of the thiol was completed by thin layer chromatography (TLC), dry ether (500 ml) was added to the reaction mixture until no more precipitate formed. Solvent was decanted, and the white precipitate was redissolved in a minimum amount of methanol (ca. 10 mL). Anhydrous diethyl ether again was added until a slight turbidity resulted (ca. 50 mL). This mixture was centrifuged, and the clear solution so obtained was removed and diluted with sufficient ether (ca. 400 mL) to precipitate the sodium salt of the disulfide sulfinate. Decantation and drying at 2.0 torr for 24 hours gave the product, a disulfide sulfinate.

Antiradiation activity of compounds of the present invention is illustrated by our compounds that led to those of the present invention; some of these are described in Gary T. Bowman et al., "Potential Antiradiation Drugs Containing No Nitrogen, and Related Compounds," *Chemico-Biological Interactions*, 57, pp. 161–174 (1986, February) which reports antiradiation activities of Compounds C and E (as VIII and XI). Earlier analogues are reported in our P. K. Srivastava, L. Field, and M. M. Grenan, "Organic Disulfides and Related Substances. 38. Some Disulfide and Trisulfide Sulfinate Salts as Antiradiation Drugs," *Journal of Medicinal Chemistry*, 18, pp. 798–802 (1975, August) and in our L. Field and Y. H. Khim "Organic Disulfides and Related Substances. 33. Sodium Related Compounds as Antiradiation Drugs," *Journal of Medicinal Chemistry*, 15, pp. 312–315 (1972) (March).

The antiradiation activity of some of the preferred compounds of the present invention was evaluated using mice, as described in detail in the Bowman et al. article.

TABLE 1

| | ANTIRADIATION EVALUATION | | | |
|---|---|---|---|---|
| Compound survival[3] | Structure (name) | Toxicity $ALD_{50}$, mg/kg, ip in mice[1,2] | Dose level mg/kg, ip | Percent |
| A | $HOCH_2CH(OH)CH_2SS$-$(CH_2)_4SO_2Na$ $1.15H_2O$ Sodium 3-(4-sulfinobutyl-dithio)-1,2-propanediol | Ca.1000 | 600 300 150 | 100 50 90 |
| C | $HO_2C(CH_2)_2SS(CH_2)_4SO_2Na$ $0.75H_2O$ Sodium 4-(2-carboxy-ethyldithio)butanesulfinate | 207 | 75 38 | 70 10 |
| E | $NaO_2S(CH_2)_4SS(CH_2)_4SS$-$(CH_2)_4SO_2Na \cdot 4H_2O$ Disodium (1,4-butylenedithio) bis(4-butane-sulfinate) | 1000 | 600 300 75 38 | 80 80 20 40 |

[1]$ALD_{50}$ = Approximate lethal dose for 50% of the 10 mice tested.
[2]Toxicity determined by the intraperitoneal route on groups of 10 mice.
[3]Based on a 30-day observation period after irradiation of 10 mice at each dose level with 10.0 Gy of γ-rays from a $^{60}Co$ source.
[4]Compound A also showed promising activity when administered orally (p.o.) as follows:

| Dose, mg/kg | Percent survival |
|---|---|
| 1200 | 30 |
| 600 | 50 |
| 300 | 60 |

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol and thus tableted or encapsulated for convenient administration; alternatively, they may be dissolved or suspended in water or a comparably innocuous liquid. Parenteral administration may be effected via sterile liquid. Parenteral administration may be effected via sterile fluid admixture with water, polyethyleneglycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example F. W. Martin et al., "Remington's Pharmaceutical Sciences", 14 Ed., Mack Publishing Company, Easton, PA., 1965.

The following examples are presented to further illustrate the present invention. They should not be construed as limiting it either in spirit or in scope. In these examples quantities are indicated in parts by weight unless parts by volume are specified, and temperatures are indicated in degrees Centigrade (°C.). The relationship between parts by weight and parts by volume is the same as that existing between grams and milliliters.

EXAMPLE 1

Sodium 3-(4-Sulfinobutyldithio)-1,2-propanediol (A)

This disulfide sulfinate A was prepared from 2.28 g (15.0 mmol) of 1,2-dithiane 1,1-dioxide, 1.08 g (10.0 mmol) of 3-mercapto-1,2-propanediol, and 230 mg (10.0 mg atom) of sodium in 10 mL of methanol; yield, 2.59 g (92%); TLC showed one spot ($R_f$ 0.58; 1:1 methanol-acetone; IR (KBr)3500–3200 (br), 2950, 1660, 1460, 1410, 1340, 1300, 1225, 1180, 1140, 1095, 1020–960, 880, 860, and 800 cm$^{-1}$; $^1$HNMR (D$_2$O) δ 4.20–3.90 (m) 3.70 (m) 3.20–2.72 (m) 2.60–2.20 (m), 2.08–1.44 (m).

Anal. Calcd for $C_7H_{15}O_4S_3Na.0.75H_2O$; C, 28.42; H, 5.61; S, 32.51. Found: C, 28.68; H, 5.18; S, 32.05. For $C_7H_{15}O_4S_3Na.1.15H_2O \rightarrow C_7H_{15}O_4S_3Na.0.75H_2O$. Calcd for H$_2$O; 2.37. Found: 2:30.

EXAMPLE 2

Sodium 3-(2-Carboxyethyldithio)propanesulfinate (B)

A solution of 1,2-dithiopane 1,1-dioxide (1.22 g, 8.84 mmol) in methylene chloride (5 mL) was added dropwise (1 min) to a stirred solution of 3-mercaptopropionic acid (0.80 g, 7.54 mmol) and sodium (0.17 g, 7.40 mg atom) in methanol (25 mL) at 5° C. After the solution was stirred for 5 min, the disulfide sulfinate salt B was precipitated by the addition of acetone (300 mL). Solvent was decanted, and the white precipitate was redissolved in a minimum amount of methanol (ca. 10 mL). Acetone (ca. 10 mL) again was added until some precipitate (ca. 10–20% of sample weight) resulted. This mixture was centrifuged, and the clear solution so obtained was removed and diluted with sufficient acetone (ca. 200 mL), to precipitate the sodium salt as the disulfide sulfinate B. Decantation and drying at reduced pressure gave 1.00 g (51%) of the titled produce B; IR (Nujol) 3700–3200 (broad), 1700, 1260, 1200, 1010, 980, 930, 720 cm$^{-1}$; $^1$H NMR (D$_2$O, DSS) δ 2.87 (m, 6), 2.46, (m, 2), 2.00 (m, 2); $^{13}$C NMR (D$_2$O, DSS) 179.86, 61.87, 40.12, 37.30, 36.11, 24.05.

Anal. Calcd for $C_6H_{11}NaO_4S_3$:C, 27.05; H, 4.17; S, 36.14. Found C, 26.84; H, 4.21; S, 35.79.

EXAMPLE 3

Sodium 4-(Carboxyethyldithio)butanesulfinate (C)

1,2-Dithiane 1,1-dioxide (3.04 g, 20 mmol) when cleaved with 3-mercaptopropionic acid (2.12 g, 20.0 mmol) and sodium (460 mg, 20 mg atom) in MeOH (20 mL) afforded 4.30 g (77%) of the titled sodium salt C: mp 188°–190° C. (dec.) $^1$HNMR (D$_2$O) δ 3.12–2.72 (m, 6H), 2.44 (t, 2H), 2.08–1.48 (m, 4H); IR (KBr) 2950, 2600–2200, 1710, 1405, 1260, 1200, 1040, 1000, 940, 900, 760, 720 cm$^{-1}$. TLC showed only one spot ($R_f$0.51; 1:1 MeOH-Me$_2$CO).

Anal. Calcd for $C_7H_{13}NaO_4S_3.0.75H_2O$; C, 28.60; H, 4.97; S, 32.73. Found: C, 29.15; H, 4.73; S, 32.14.

EXAMPLE 4

Sodium 5-(2-Carboxyethyldithio)pentanesulfinate (D)

A solution of 1,2-dithiepane 1,1-dioxide (1.10 g, 6.63 mmol) in CH$_2$Cl$_2$ (5 mL) was added dropwise (2 min) to a stirred solution of 3-mercaptopropionic acid (0.562 g, 5.30 mmol) and sodium (0.122 g, 5.30 mg atom) in methanol (35 mL) at ambient temperature. After addition, the solution was stirred for 2 min., at which time the disulfide sulfinate D was precipitated by the addition of ether (350 mL). Solvent was decanted, and the white precipitate was redissolved in a minimum amount of methanol (ca. 10 mL). Ether (ca. 10 mL) again was added until some turbidity (ca. 10–20% of sample weight) resulted. This mixture was centrifuged, and the clear solution so obtained was removed and diluted with sufficient ether (ca. 20 mL) to precipitate the sodium salt as the disulfide sulfinate D. Decantation and drying at reduced pressure gave 0.91 g (58%) of the product D: IR (Nujol) 3900–3200 (broad), 1700, 1040, 1030, 1000, 980, 720 cm$^{-1}$; $^1$H NMR (D$_2$O, DSS) δ 2.76, (m, 6), 2.36 (t, 2), 1.57 (m, 6); $^{13}$C NMR (D$_2$O, DSS) δ 180.51, 63.30, 40.74, 37.81, 36.38, 30.61, 29.63, 23.78.

Anal. Calcd for $C_8H_{15}NaO_4S_3.0.35H_2O$; C, 31.94; H, 5.22; S, 32.00. Found: C 31.76; H, 4.66; S, 32.10.

EXAMPLE 5

Disodium (1,4-Butylenedithio)bis(4-butanesulfinate) (E)

Sodium (230 mg, 10 mg atoms) dissolved in methanol (15 mL) was added dropwise to a mixture of 1,2-dithiane 1,1-dioxide (1.52 g, 10 mmol) and 1,4-butanedithiol (0.61 g, 5.0 mmol) in methanol. Isolation by precipitation and reprecipitation as usual afforded 2.0 g (74% based on the tetrahydrate of the titled salt E.) Thin layer chromatography (TLC) showed one spot ($R_f$ 0.54: 1:1 methanol-acetone). Additional TLC spots appeared in 5 min. or less after dissolution of the disulfide sulfinate E in H$_2$O, the solution became turbid, and the $1_H$NMR spectrum (D$_2$O) changed. IR (KBr) 3400, 2950, 1660, 1440, 1220, 1000 (br), 980, 800, 720 cm$^{-1}$; NMR (D$_2$O δ 3.40–2.64 (m, 8H), 2.60–2.20 (m, 4H), 2.04–1.40 (m, 12H).

Anal. Calcd for $C_{12}H_{24}Na_2O_4S_6.4H_2O$: C, 26.55; H, 5.94; S, 35.44. Found: C, 26.06; H, 5.15; S, 34.80.

What is claimed is:

1. A compound of the formula

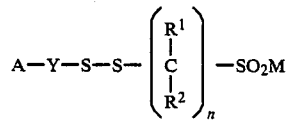

wherein A is COOH, Y is a straight chain alkyl having from two to eight carbon atoms which may have an S-S group interposed therebetween, R$^1$ and R$^2$ are hydrogen or cycloalkyl, n is an integer from two through five, M is hydrogen, alkali metal or a straight chain alkyl having up to four carbon atoms.

2. Sodium 3-(2-carboxyethyldithio)propanesulfinate.
3. Sodium 4-(2-carboxyethyldithio)butanesulfinate.
4. Sodium 5-(2-carboxyethyldithio)pentanesulfinate.

* * * * *